(12) United States Patent
Lee et al.

(10) Patent No.: US 8,968,674 B2
(45) Date of Patent: Mar. 3, 2015

(54) FLUID SENSOR PREVENTING GENERATION OF AIR BUBBLES

(75) Inventors: Hun Joo Lee, Hwaseong-si (KR); Soo Suk Lee, Suwon-si (KR); Jung Nam Lee, Incheon (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 674 days.

(21) Appl. No.: 13/037,415

(22) Filed: Mar. 1, 2011

(65) Prior Publication Data

US 2012/0015451 A1 Jan. 19, 2012

(30) Foreign Application Priority Data

Jul. 13, 2010 (KR) ................. 10-2010-0067146

(51) Int. Cl.
*G01N 21/75* (2006.01)
*G01N 31/22* (2006.01)
*G01N 33/52* (2006.01)
*G01N 29/22* (2006.01)
*G01N 29/02* (2006.01)

(52) U.S. Cl.
CPC ............ *G01N 29/222* (2013.01); *G01N 29/022* (2013.01); *Y10S 436/807* (2013.01)
USPC ............ 422/401; 422/50; 422/400; 422/68.1; 422/82.05; 436/501; 436/518; 436/807; 435/283.1; 435/287.2; 435/287.9; 435/288.3; 435/288.7

(58) Field of Classification Search
USPC ........ 422/401, 50, 400, 68.1, 82.05; 436/501, 436/518, 807; 435/283.1, 287.2, 287.9, 435/288.3, 288.7
See application file for complete search history.

(56) References Cited

U.S. PATENT DOCUMENTS

| | | | | |
|---|---|---|---|---|
| 5,234,813 | A | * | 8/1993 | McGeehan et al. ............ 435/7.9 |
| 5,922,604 | A | * | 7/1999 | Stapleton et al. ............... 436/46 |
| 6,576,478 | B1 | * | 6/2003 | Wagner et al. .................. 506/32 |
| 8,231,844 | B2 | * | 7/2012 | Gorfinkel et al. ............. 422/502 |
| 2002/0006664 | A1 | * | 1/2002 | Sabatini ........................ 435/456 |
| 2007/0161051 | A1 | * | 7/2007 | Tsinberg et al. ............... 435/7.2 |
| 2007/0269893 | A1 | * | 11/2007 | Blankenstein et al. ........... 436/2 |
| 2010/0167337 | A1 | * | 7/2010 | Tsinberg et al. ................ 435/29 |

FOREIGN PATENT DOCUMENTS

| | | |
|---|---|---|
| JP | 2007111672 A | 5/2007 |
| JP | 2008203003 A | 9/2008 |
| JP | 2008298598 A | 12/2008 |
| JP | 2009236555 A | 10/2009 |

OTHER PUBLICATIONS

Adhesion of Oral Streptococci from a Flowing Suspension to Uncoated and Albumin-coated Surfaces; I N A H. Pratt-Terpstra, Anton H . Weerkamp and Henk J . Busscher; Journal of General Microbiology (1987), 133, 3199-3206.

* cited by examiner

*Primary Examiner* — Melanie Y Brown
(74) *Attorney, Agent, or Firm* — Leydig, Voit & Mayer, Ltd.

(57) ABSTRACT

Provided herein is a fluid sensor, which includes a closed reaction unit in which reaction of a fluid sample takes place. The reaction unit is tapered on a side through which the fluid is injected so as to prevent generation of air bubbles during the injection of the fluid. Thus, the sensor has improved sensitivity.

8 Claims, 4 Drawing Sheets

FLUID SENSOR PREVENTING GENERATION OF AIR BUBBLES

CROSS-REFERENCE TO RELATED APPLICATION

This application claims priority to Korean Patent Application No. 10-2010-0067146, filed on Jul. 13, 2010, and all the benefits accruing therefrom under 35 U.S.C. §119, the content of which in its entirety is herein incorporated by reference.

BACKGROUND

1) Field

This disclosure relates to a fluid sensor, more particularly, to a fluid sensor for preventing air bubble generation when sensing the fluid, thereby increasing the fluid sensor's sensitivity.

2) Description of the Related Art

A sensor is a device that responds to a stimulus and correspondingly emits an impulse signal, which can be subsequently read by an observer or an instrument. Some sensors are used for sensing and measuring active materials or physical changes resulting from the reaction of a target material upon contact with an electrical, a physical or a chemical device. One type of such a sensor is a fluid sensor, which senses for presence of a certain target material in a fluid. An example of a fluid sensor is a biosensor, which detects the presence of a target material in a bio sample by immobilizing, on a certain substrate, a receptor material that specifically binds to the target material. Subsequently, the bio sample containing the target material flows on the surface of the sensor, which outputs a signal for reading by an observer or an instrument.

Mass sensors, which typically measure a change in a sensor surface mass, are sensitive to fluid pressure and viscosity and density of a medium. For example, when the sensed sample is a solution, the mass sensor is highly affected by the solution's pressure, viscosity and density, resulting in generation of a noise, which is greater than a sensing signal. Hence, the mass sensor cannot be properly operated. Particularly, due to the structure of a current sensing chamber in a mass sensor, air bubbles are often generated in the solution, leading to changes in the sensor surface pressure and the viscosity and density of the solution. The signal noise resulting from air bubble generation thus prevents the mass sensor from functioning properly.

SUMMARY

Disclosed herein is a fluid sensor which includes a structure capable of substantially preventing and/or effectively minimizing air bubble generation or substantially removing air bubbles. The fluid sensor effectively minimizes signal noise, thus improving the fluid sensor sensitivity and ensuring the fluid sensor reliability.

In an embodiment, the fluid sensor includes a main body including an underlying substrate and a top plate disposed thereon, a reaction unit including an inner space of the main body in which reaction of a fluid sample takes place, and an inlet disposed on a first top plate side of the top plate to inject a fluid sample into the reaction unit and an outlet disposed on the other side of the top plate to exhausts the fluid sample from the reaction unit. A side cross-section of a region (A) of the reaction unit including the inlet includes a slope tapered at a positive angle ($\alpha$).

In an embodiment, angle ($\alpha$) of the slope may be less than a contact angle of the substrate.

In an embodiment, a top of the slope may be rounded or flat and a vertical cross-section of the reaction unit may be formed in a quadrilateral shape, a rounded shape or a flat shape inwardly tapered on both sides. A horizontal cross-section of the reaction unit including the slope may also be formed in a quadrilateral shape, a rounded shape or a flat shape inwardly tapered on both sides. An inwardly tapering angle ($\beta$) may be less than the contact angle of the substrate.

In an embodiment, a lower side of the inlet may be adjacent to the substrate and a lower side of the outlet may be disposed at approximately the same level as an inner side of the top plate disposed on the substrate.

In an embodiment, a side cross-section of a region (B) of the reaction unit including the outlet may include a slope tapered at a positive angle ($\theta$).

In an embodiment, a fluid sensor may be used as a surface plasmon resonance ("SPR") sensor, a quartz crystal microbalance ("QCM") sensor, a cantilever sensor, a surface acoustic wave ("SAW") sensor or a bulk acoustic wave ("BAW") sensor.

BRIEF DESCRIPTION OF THE DRAWINGS

The above and other aspects, advantages and features of the invention will become more readily apparent by describing in further detail embodiments thereof which reference to the accompanying drawings, in which.

DETAILED DESCRIPTION

Figure 1:
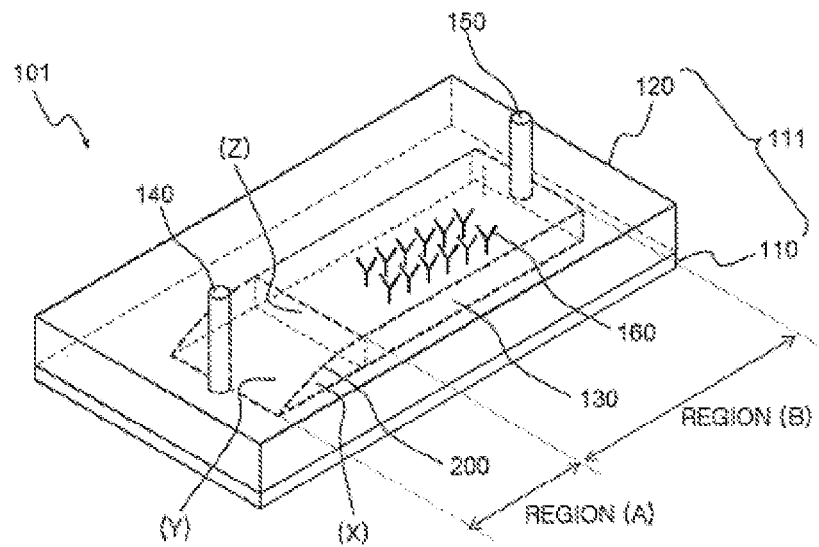
FIG. 1 is a diagram illustrating an embodiment of a chamber of a fluid sensor.

The invention now will be described more fully hereinafter with reference to the accompanying drawings, in which various embodiments are shown. This invention may, however, be embodied in many different forms and should not be construed as limited to the embodiments set forth herein. Rather, these embodiments are provided so that this disclosure will be thorough and complete and will fully convey the scope of the invention to those of ordinary skill in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated regions, integers, steps, operations, elements, and/or components, but do not preclude the presence or addition of one or more other regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein, but are to include deviations in shapes that result, for example, from manufacturing. For example, a region illustrated or described as flat may, typically, have rough and/or nonlinear portions. Moreover, sharp angles that are illustrated may be rounded. Thus, the regions illustrated in the figures are schematic in nature and their shapes are not intended to illustrate the precise shape of a region and are not intended to limit the scope of the present claims.

In a fluid sensor for detecting a fluid sample, a reaction generally occurs on a substrate on which a marker, which specifically binds to a target biomolecule, is immobilized. The fluid sensor includes a chamber, which is a closed system, to prevent evaporation and contamination of a liquid. While the entire area of a reaction unit needs to be wet when the fluid sample is injected into the reaction unit, a certain area is not wet due to a difference in a contact angle, resulting in air bubble generation and signal noise. Thus, disclosed herein is a fluid sensor including a structure capable of easily removing generated air bubbles.

Hereinafter, various embodiments will be described more fully with reference to the accompanying drawings in which some embodiments are shown. In the drawings, the thicknesses of layers and regions may be exaggerated for clarity.

FIG. 1 is a diagram illustrating an embodiment of a chamber of a fluid sensor.

Referring to FIG. 1, the chamber 101 of the fluid sensor includes a main body 111 including an underlying substrate 110 and a top plate 120 disposed thereon. An inner space of the main body 111 corresponds to a reaction unit 130 in which a fluid sample reaction takes place.

In an embodiment, to detect a target material included in a fluid sample, a receptor 160 specifically binding to the target material is immobilized in an area of the substrate 110 included in the reaction unit 130. In an embodiment, the fluid sample is a biological sample, such as saliva, sputum, cerebrospinal fluid, blood, serum, plasma, urine or a biopsy sample. Some examples of target materials include, but are not limited to, biomolecules, such as proteins, antibodies, antigens, a deoxyribonucleic acid ("DNA"), a ribonucleic acid ("RNA"), viruses, bacterial cells, animal cells and tissues, and bio products, such as toxins produced therefrom.

In an embodiment, the receptor 160 specifically binds to the target material, which is a protein, an antigen, an antibody, a DNA molecule, a RNA molecule, peptide nucleic acid ("PNA"; artificial DNA), a cell or an olfactory cell.

In an embodiment, the receptor 160 is directly bound to the substrate 110 or be immobilized on another plate and then disposed onto the substrate 110. In an embodiment, the substrate 110 is suitably selected depending on the adhesive power of the receptor 160 and characteristics and mechanical properties of the sensor. In an embodiment, the substrate 110 is one of various kinds of substrates known in the art, such as a silicon substrate, a plastic substrate, a semiconductor substrate and a glass substrate. In an embodiment, a piezoelectric material is used to form the substrate 110 depending on a type of the fluid sensor. Generally, the piezoelectric material is a material whose electrical characteristic is converted when a mechanical signal is applied (the piezoelectric effect) or a material capable of generating a mechanical signal when an electrical signal is applied (the reverse piezoelectric effect). Some examples of piezoelectric materials include lithium niobate ($LiNbO_3$), lithium tantalite ($LiTaO_3$), lithium tetraborate ($Li_2B_4O_7$), barium titanate ($BaTiO_3$), $PbZrO_3$, $PbTiO_3$, PZT, ZnO, GaAs, quartz and niobate.

In an embodiment, the top plate 120 is manufactured out of a different material than the substrate 110. In an embodiment, when both the top plate 120 and the substrate 110 are manufactured out of the same material, then the top plate and the substrate 110 have the same contact angle, thus resulting in uniform wetting of the top plate 120 and the substrate 110. In an embodiment, the top plate 120 is manufactured out of a hydrophobic material for a rubber gasket or a polymer resin to prevent leakage of the fluid sample or a hydrophilic material. In an embodiment, when the substrate 110 and the top plate 120 are manufactured out of the same material, then wetting caused by a difference in the contact angle between the substrate 110 and the top plate 120 is substantially prevented, thereby substantially reducing and/or effectively minimizing air bubble generation.

In an embodiment, a closed inner space formed by the substrate 110 and the top plate 120 is the reaction unit 130. To input or output the fluid sample into or from the reaction unit 130, an inlet 140, through which the fluid sample is input, penetrates one side of the top plate 120 and an output 150, through which the fluid sample is exhausted from the reaction unit 130, penetrates the other side of the top plate 120.

In an embodiment, if necessary, a pump for providing driving power for moving the fluid sample and a valve for controlling the input and output of the fluid is connected to the inlet 140 and the outlet 150. In an embodiment, a positive pressure pump is connected to the inlet 140 and a negative pressure pump is connected to the outlet 150. Consequently, when the valve for the inlet 140 is open, then air exhausted from the positive pressure pump for the inlet 140 is input into the reaction unit 130 and using a pressure generated thereby, the fluid sample is moved. When the valve for the outlet 150 is open, then a pressure in the reaction unit 130 is decreased due to the negative pressure pump for the outlet 150 and thus the fluid sample moves to the outlet 150.

Hereinafter, for clarity, an area of the reaction unit 130 including the inlet 140 is referred to as a region A and an area of the reaction unit 130 including the outlet 150 is referred to as a region B.

In an embodiment, in the region A, the fluid sample input through the inlet 140 spreads to the reaction unit 130. Upon coming in contact with the substrate 110, the fluid sample spreads to the reaction unit 130 on a surface of the substrate 110. At this time, the fluid sample is in contact with the top plate 120. If the fluid is not completely adhered to the top plate 120, then a certain area of the reaction unit 130 is not fully wet and air bubbles are thus generated. Though sometimes a very small amount of air bubbles is not significant, air bubbles often accumulate to generate a large air bubble, resulting in generation of signal noise.

Figure 2:
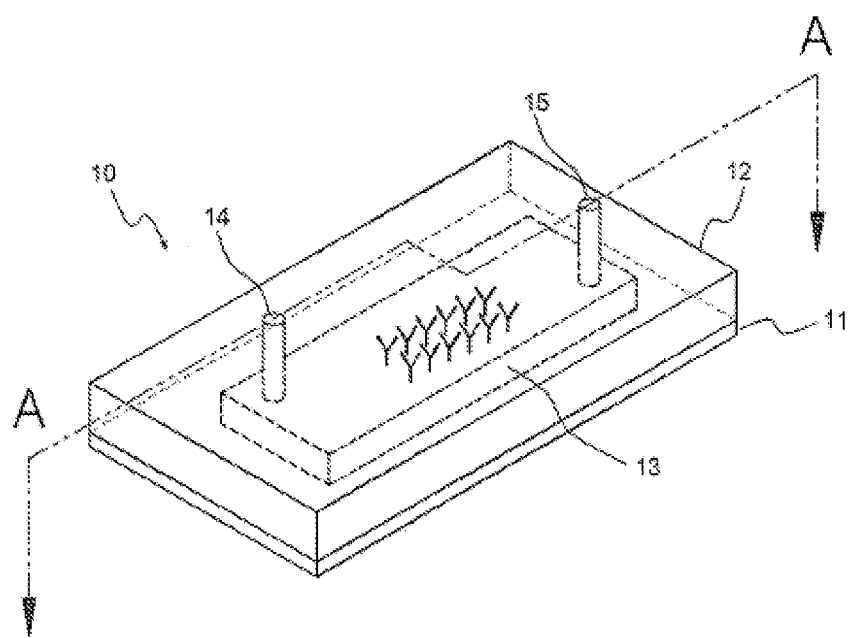
FIG. 2 is a diagram of a chamber of a conventional fluid sensor.
Figure 3:
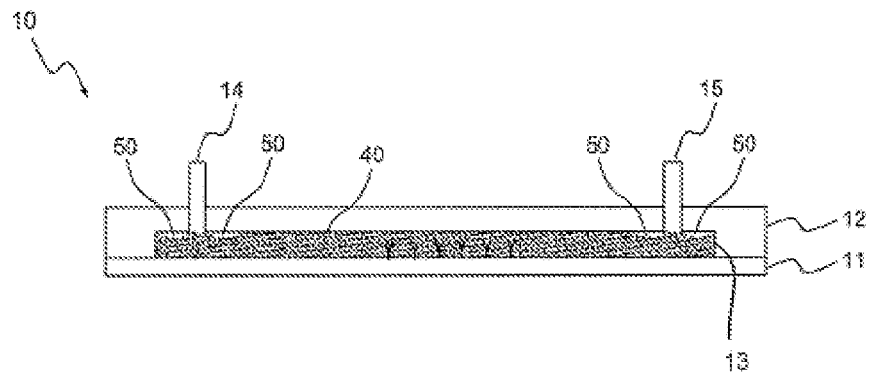
FIG. 3 is a vertical cross-sectional view, taken along line A-A, which illustrates the chamber of the conventional fluid sensor of FIG. 2.

FIGS. 2 and 3 are perspective and vertical cross-sectional views of a conventional fluid sensor 10. Referring thereto, a reaction unit 13 is formed in the shape of a cuboid and an inlet 14 and an outlet 15 penetrate a top plate 12. When the fluid 40 is injected through the inlet 14, the fluid 40 is initially in contact with the substrate 11, but cannot be in contact between the substrate 11 and the top plate 12 in an area 50. Thus, air bubbles are generated.

Referring back to FIG. 1, to prevent air bubble generation, a cross-section X of the region A has a slope 200 tapered at a positive angle α, thus reducing or even preventing air bubble generation in the reaction unit 130. Specifically, in an embodiment, the entire area of the top plate 120 is wet by the solution in contact with the substrate 110 without air bubbles. Further, a fluid moving distance is reduced and rapid acceleration is provided during the fluid movement.

Figure 8:
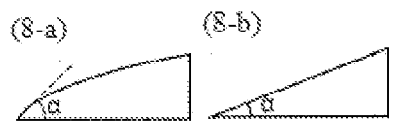
FIG. 8-*a* and FIG. 8-*b* are diagrams illustrating embodiments of various slope shapes.

In an embodiment, the slope angle α is less than the substrate contact angle and the slope 200 is rounded as shown in FIG. 8-a or flat as shown in FIG. 8-b.

In an embodiment, the substrate contact angle is an angle at which a liquid surface meets a solid planar surface. The substrate contact angle is determined by coherence between liquid molecules and adhesion between liquid and solid walls. Thus, depending on a substrate type, the contact angle is alterable.

In an embodiment, when the slope 200 is inclined at an angle less than the substrate contact angle, then the liquid input into the reaction unit 130 does not generate liquid drops, but spreads to the reaction unit 130.

In an embodiment, a vertical cross-section Z of the reaction unit 130 is formed in a quadrilateral shape, a rounded shape or a flat shape inwardly-tapered on both sides. In an embodiment, a horizontal cross-section Y of the reaction unit 130 is formed in a quadrilateral shape, a rounded shape or a flat shape inwardly-tapered on both sides. Since, an inwardly-tapering angle is less than the substrate contact angle, the fluid spreads into the reaction unit 130 without cohering, thus wetting the entire area of the top plate 120, thereby preventing air bubble generation.

Figure 9:
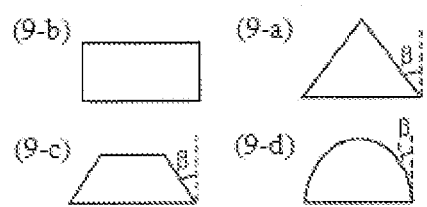
FIGS. 9-*a* to 9-*d* are diagrams illustrating embodiments of various shapes of horizontal and vertical cross-sections of a reaction unit.

In an embodiment, the horizontal cross-section Y or the vertical cross-section Z is formed in a quadrilateral shape as shown in FIG. 9-b, a triangular shape as shown in FIG. 9-a, a trapezoidal shape as shown in FIG. 9-c or a semicircular shape as shown in FIG. 9-d. Additionally, in an embodiment, the horizontal cross-section Y or the vertical cross-section Z is formed in a polygonal shape or an amorphous shape.

Figure 4:
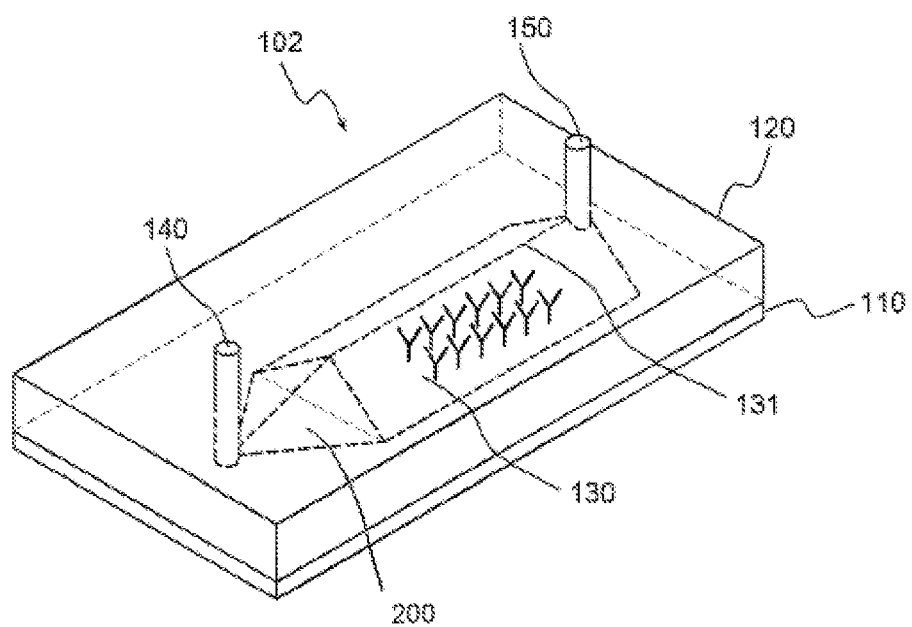
FIG. 4 is a diagram illustrating another embodiment of a chamber of a fluid sensor.
Figure 5:
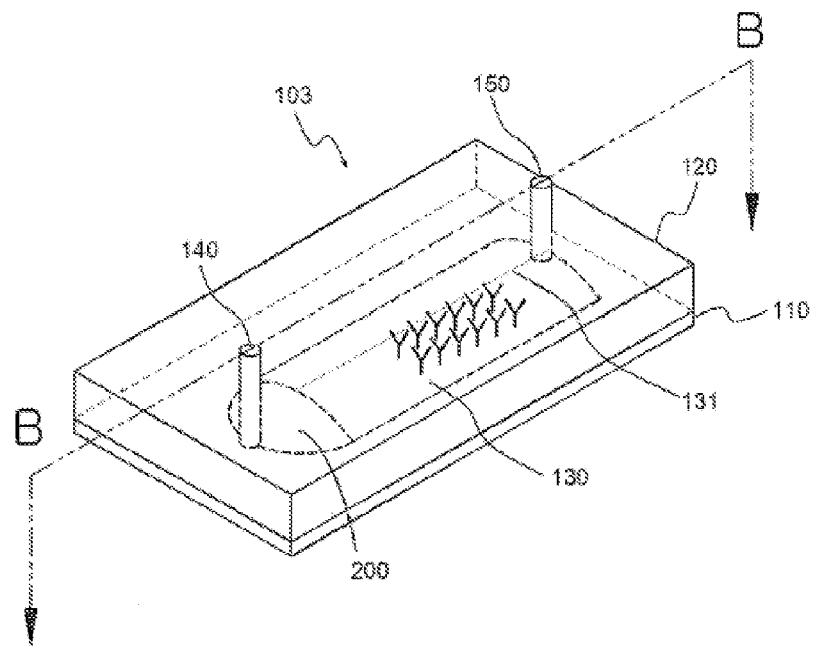
FIG. 5 is a diagram illustrating another embodiment of a chamber of a fluid sensor.
Figure 6:
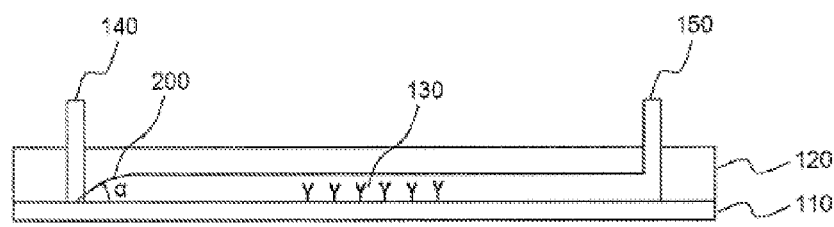
FIG. 6 is a vertical cross-sectional view, taken along line B-B, which illustrates the chamber of the fluid sensor of FIG. 5.

FIG. 4 is a perspective view of another embodiment of a fluid sensor. FIGS. 5 and 6 are perspective and cross-sectional views of another embodiment of a fluid sensor. For clarity, in FIGS. 4 to 6, like numerals refer to like or corresponding components as in FIG. 1.

In the embodiment of FIG. 1, the vertical cross-section Z and horizontal cross-section Y are square shaped.

In the embodiments of FIGS. 4 and 5, both sides of the reaction unit 130 taper inwardly and the vertical cross-section Z and the horizontal cross-section Y are differently shaped. The fluid sample is input into the reaction unit 130 via the inlet 140, eventually concentrated in a central area 131, which is disposed at a relatively high level of the reaction unit 130, and easily exhausted via the outlet 150. Consequently, even if air bubbles are generated in the reaction unit 130, the air bubbles can be easily removed.

In the embodiment of FIG. 4, in a chamber 102, both sides of the vertical cross-section Z taper inwardly and are in a polygonal shape, such as a triangle or a trapezoid.

In the embodiment of FIG. 5, in a chamber 103, both sides of the vertical cross-section Z taper inwardly and are in a semicircular shape. Since there are no corners, the generation of air bubbles is substantially prevented and/or effectively minimized and the fluid sample is easily exhausted without capturing generated air bubbles.

Referring to FIGS. 1 and 4 through 6, the inlet 140 is in contact with or adjacent to the substrate 110 in order to facilitate the contact between the fluid sample and the substrate 110. The outlet 150 is adjacent to or formed on the top plate 120 in order to facilitate exhaustion of the fluid sample.

Figure 7:
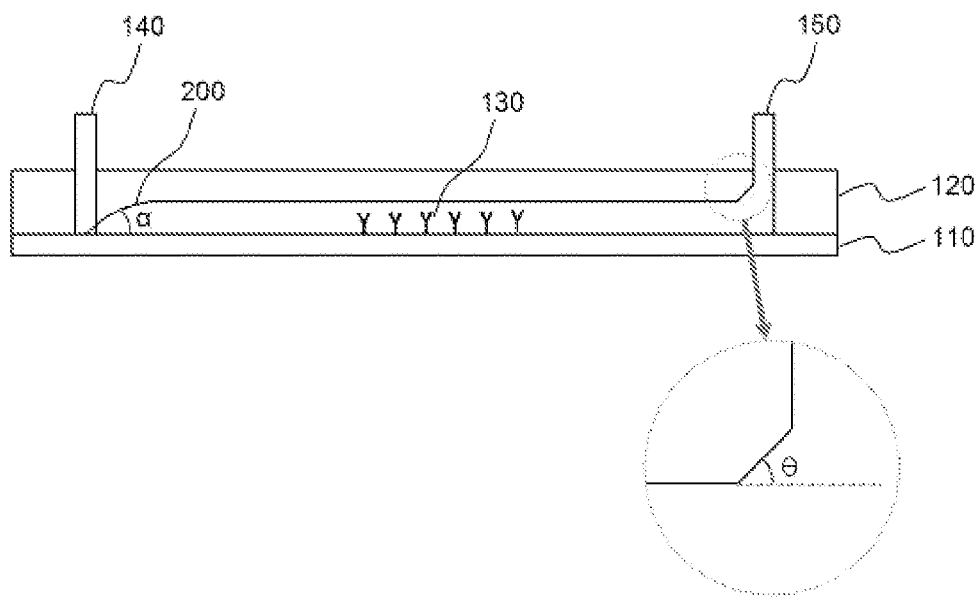
FIG. 7 is a vertical cross-sectional view illustrating an embodiment of a transformed structure of an outlet of FIG. 6.

FIG. 7 illustrates a vertical cross-sectional view illustrating another embodiment of a transformed structure of an outlet of FIG. 6. The side cross-section of region B of the reaction unit 130 including the outlet 150 has a slope tapered at a positive angle θ. As previously described, since the outlet 150 is formed at a higher level than the reaction unit 130, air bubbles generated by fluid sample reaction or movement are easily removed.

A method by which the fluid sensors described herein are operated is not limited to the described fluid sensors. Minimally, the method is applicable to a surface plasmon resonance ("SPR") sensor, a quartz crystal microbalance ("QCM") sensor, a cantilever sensor, a surface acoustic wave ("SAW") sensor or a bulk acoustic wave ("BAW") sensor.

Generally, the SPR sensor measures a degree of adsorption of a sample on a surface of a metal, such as gold or silver, or a metal nanoparticle. SPR refers to a state of a surface plasmon excited by light incident onto a planar surface.

Generally, the QCM sensor measures a concentration of a target material by immobilizing a receptor on a quartz crystal coated with a coupling agent, facilitating a reaction of the receptor with a certain material to be measured and measuring a variation in frequency before and after the reaction.

Generally, the cantilever sensor measures static deflection by using bending of a cantilever caused by changes in resonance frequency and stress when molecules are adsorbed onto the surface of the cantilever.

Generally, the SAW sensor and the BAW sensor sense the presence or properties of a target material using an acoustic wave propagated as an elastic wave in a solid. In contrast to an electromagnetic wave, the acoustic wave is a mechanical wave generated by movement of particles by external thermal, mechanical and/or electrical forces where a large portion of vibrational energy is concentrated on the surface of a medium. BAW is propagated through the bulk of an elastic substrate and SAW is propagated along the surface of the substrate.

In an embodiment, a SAW biosensor including a structure as shown in FIG. 5 includes a $SiO_2$ substrate 110 coated with bovine serum albumin. A self assembled-monolayer ("SAM") layer is formed of (3-aminopropyl)-triethoxysilane ("APTES") on a surface of the $SiO_2$ substrate covered by the top plate 120. The slope angle ($\alpha$) is about 40 degrees less than the substrate contact angle, i.e., about 59 degrees (see Journal of General Microbiology (1987), 133, 3199-3206). The top plate 120 is manufactured out of silicon. The substrate has a depth of 2.5 millimeters (mm), a width of 8.4 mm and a height of 1 mm. The inlet 140 is used for input of a fluid sample to be in direct contact with the substrate 110. The outlet 150 is used for fluid sample exhaustion. Both the inlet 140 and the outlet 150 are of a diameter of 0.7 mm. A pair of inter-digital transducers ("IDTs") for the SAW sensor is formed on the substrate 110. A top of the top plate 120 is connected to a tube coupled with a pump and a valve In an embodiment, a liquid sample, 1× phosphate buffered saline ("PBS"), is injected into a SAW biosensor including a structure as shown in FIG. 1 and the immediately previously described biosensor including a slope angle ($\alpha$) at about 40 degrees less than the substrate contact angle. The liquid sample is injected through the inlet 140 at 1 milliliter per minute (ml/min) at room temperature. The liquid sample is exhausted via the outlet 150 and air bubble frequency is manually observed. Noise frequency is determined by measuring frequency shift in hertz (Hz) during the reaction.

As subsequent Table 1 shows, in the SAW biosensor including a slope angle ($\alpha$) at about 40 degrees less than the substrate contact angle, the entire region of the top plate is wet and air bubbles are not generated. Hence, no noise caused by the air bubbles is generated. The SAW biosensor including a slope angle ($\alpha$) at about 40 degrees less than the substrate contact angle exhibits a dramatically lower noise rate than the conventional noise rate of 30%.

TABLE 1

|  | Conventional SAW Biosensor | SAW Biosensor including a slope angle ($\alpha$) at about 40 degrees less than the substrate contact angle) |
|---|---|---|
| Operation Time | 30 | 30 |
| Air Bubble Frequency | 19 | 0 |

TABLE 1-continued

|  | Conventional SAW Biosensor | SAW Biosensor including a slope angle ($\alpha$) at about 40 degrees less than the substrate contact angle) |
|---|---|---|
| Noise Frequency | 10 | 0 |
| Noise Rate | 30% | 0% |

The invention should not be construed as being limited to the embodiments set forth herein. Rather, these embodiments are provided so that this disclosure will be thorough and complete and will fully convey the invention to those of ordinary skill in the art.

In addition, while the invention has been particularly shown and described with reference to embodiments thereof, it will be understood by those of ordinary skill in the art that various changes in form and details may be made therein without departing from the spirit or scope of the invention concept as defined by the following claims.

What is claimed is:

1. A fluid sensor comprising:
a main body comprising:
an underlying substrate and a top plate disposed thereon,
a reaction unit including an inner space of the main body,
an inlet disposed in a first side of the top plate and fluidly connected to the reaction unit; and
an outlet disposed in a second side of the top plate and fluidly connected to the reaction unit, the lower side of the outlet being disposed on the top plate,
wherein the reaction unit has a side profile from a vertical cross-section in a direction from the inlet to the outlet that includes a slope at a positive angle ($\alpha$) to the underlying substrate that is less than a contact angle of the substrate, which tapers the inner space of the reaction unit towards the inlet, and
the vertical cross-section of the reaction unit in a direction perpendicular to the direction from the inlet to the outlet, and a horizontal cross-section of the reaction unit, have a shape that is inwardly tapered on both sides, with an inwardly tapered angle ($\beta$) that is less than a contact angle of the substrate.

2. The sensor of claim 1, wherein a top of the slope is rounded or flat.

3. The sensor of claim 1, wherein a vertical cross-section of the reaction unit in a direction perpendicular to the direction from the inlet to the outlet has a quadrilateral shape, a rounded shape or a flat shape inwardly tapered on both sides.

4. The sensor of claim 1, wherein a horizontal cross-section of the reaction unit has a quadrilateral shape, a rounded shape or a flat shape inwardly tapered on both sides.

5. The sensor of claim 1, further comprising a receptor that specifically reacts with a target material in the fluid sample, the receptor immobilized on at least a portion of a substrate area in the reaction unit.

6. The sensor of claim 1, wherein a lower side of the inlet is in contact with or adjacent to the substrate.

7. The sensor of claim 1, wherein the side view profile of the reaction unit from a vertical cross-section in a direction from the inlet to the outlet includes a second slope at a positive angle ($\theta$) to the underlying substrate, which tapers the inner space of the reaction unit towards the outlet.

8. The sensor of claim 1, wherein the sensor is one of a surface Plasmon resonance sensor, a quartz crystal microbalance sensor, a cantilever sensor, a surface acoustic wave sensor and a bulk acoustic wave sensor.

* * * * *